United States Patent
Nurminen et al.

(10) Patent No.: US 8,747,772 B2
(45) Date of Patent: Jun. 10, 2014

(54) DEVICE FOR BATCH TREATMENT

(75) Inventors: Teppo Nurminen, Ojakkala (FI); Ilkka Laitinen, Gammelby (FI)

(73) Assignee: Steris Europe, Inc. Suomen Sivuliike, Tuusula (FI)

( * ) Notice: Subject to any disclaimer, the term of this patent is extended or adjusted under 35 U.S.C. 154(b) by 796 days.

(21) Appl. No.: 12/448,117

(22) PCT Filed: Dec. 13, 2007

(86) PCT No.: PCT/FI2007/050689
§ 371 (c)(1),
(2), (4) Date: Jan. 15, 2010

(87) PCT Pub. No.: WO2008/071853
PCT Pub. Date: Jun. 19, 2008

(65) Prior Publication Data
US 2010/0143218 A1    Jun. 10, 2010

(30) Foreign Application Priority Data

Dec. 13, 2006 (FI) ...................................... 20065798

(51) Int. Cl.
*A61L 9/00* (2006.01)
*B01J 7/00* (2006.01)
*A61L 2/00* (2006.01)

(52) U.S. Cl.
USPC ............................ 422/306; 422/292; 422/295

(58) Field of Classification Search
USPC .......................... 422/292, 295, 300, 305, 306
See application file for complete search history.

(56) References Cited

U.S. PATENT DOCUMENTS

| 2,713,702 | A | | 7/1955 | Jewell | 21/98 |
| 3,150,935 | A | | 9/1964 | Matteson | 422/105 |
| 3,180,738 | A | * | 4/1965 | Lassen | 426/524 |
| 3,259,466 | A | | 7/1966 | Jacks, Jr. | 422/53 |
| 4,193,818 | A | * | 3/1980 | Young et al. | 134/1 |
| 4,226,642 | A | * | 10/1980 | Baran | 134/10 |
| 4,782,214 | A | * | 11/1988 | Voegtlin | 219/401 |

(Continued)

FOREIGN PATENT DOCUMENTS

| DE | 19707291 | | 8/1998 | |
| EP | 03333389 | | 9/1989 | |
| JP | 01219421 | A * | 9/1989 | F24C 7/02 |

OTHER PUBLICATIONS

Int'l Search Report (from PCT/FI2007/050689), Apr. 22, 2008, 3 pages.

*Primary Examiner* — Regina M Yoo
(74) *Attorney, Agent, or Firm* — Kusner & Jaffe; Michael A. Centanni

(57) ABSTRACT

The invention relates to the batch treatment of goods with gas, steam or vapor, for example sterilization and drying. The distribution of the medium surrounding the load (8) during all stages of such a process is important. According to the invention, movement of fluids within a batch treatment apparatus is achieved using a fluid ejector device (9), An apparatus for the gas, steam or vapor treatment of objects is provided, said apparatus having inside a closable chamber (1) at least one ejector device (9) of the type having a straight flow path for the secondary stream. Any particular fluid or mixture of different fluids entering the chamber during a treatment process may be introduced via an ejector device (9) in order to distribute the fluid around the load (8), or remove material deposited on the load (8). The invention eliminates the need for shaft seal arrangements involved with fans.

3 Claims, 1 Drawing Sheet

(56) References Cited

U.S. PATENT DOCUMENTS

| | | | |
|---|---|---|---|
| 4,830,278 A | 5/1989 | Kohmura et al. | 99/468 |
| 4,935,604 A * | 6/1990 | Allen et al. | 219/400 |
| 5,027,615 A * | 7/1991 | Wakatsuki et al. | 62/419 |
| 5,185,126 A * | 2/1993 | Adamski et al. | 422/38 |
| 5,451,744 A * | 9/1995 | Koopman et al. | 219/400 |
| 5,524,653 A * | 6/1996 | Minkin et al. | 134/102.2 |
| 5,873,256 A * | 2/1999 | Denniston | 62/91 |
| 6,293,121 B1 * | 9/2001 | Labrador | 62/304 |
| 6,391,259 B1 | 5/2002 | Malkin et al. | 422/28 |
| 7,658,891 B1 * | 2/2010 | Barnes | 422/186.03 |
| 2005/0089458 A1 * | 4/2005 | Oke | 422/207 |
| 2005/0260097 A1 | 11/2005 | Williams et al. | 422/28 |
| 2006/0032258 A1 * | 2/2006 | Pruitt et al. | 62/310 |

* cited by examiner

DEVICE FOR BATCH TREATMENT

FIELD OF THE INVENTION

The invention relates to the batch treatment of products enclosed in a chamber. In particular, the invention relates to an arrangement for the circulation of gases, steam or vapor within the chamber for improving heat transfer, fluid penetration or material transfer.

BACKGROUND OF THE INVENTION

Sterilization of goods may be carried out in batch processes, wherein a number of goods, called the load, is loaded into a chamber of appropriate size and subjected, e.g., to a temperature cycle ensuring a specified degree of sterility, that is lack of viable microorganisms. Chemicals may also be employed, e.g. the use of peroxides and ethylene oxide are well known, but the majority of such sterilization processes work by means of heating, often with steam. With steam in this context, and for the purpose of this text, is meant water in gaseous form or condensing at its dew point. Vapor for the purpose of this text means liquid dispersed in a gas.

Sterilization processes often include rinsing, cooling or drying stages, typically using clean air.

The apparatus employed has developed from the traditional simple autoclave to advanced, GMP-validated sterilizers programmable for a multitude of different tasks.

The specific process used for a particular sterilization task is dependent on the characteristics of the load. Solid materials, which may be porous or have a complicated structure may be subjected to a vacuum, which assists in replacing the initial surrounding atmosphere with heat transfer medium. Other loads, like liquids packed in vented containers or bottles, vials, ampoules, pouches, blister pads and the like, may not tolerate vacuum and must be heat treated at pressures from atmospheric upwards.

As the heat stability of many types of loads is limited, and also due to economical reasons, the load must often be cooled when the specified amount of heat has been delivered. Thus, the processes routinely include stages of active cooling. If the load must be dry when leaving the sterilization process, this also requires tailoring of the procedures.

It is a well-known physical fact that convection is a more efficient mechanism in heat transfer than conduction. Also, the conditions within a sterilization chamber must be as uniform as possible to ensure sterilization efficiency regardless of the location and shape of a particular piece of load. Thus, the distribution of the medium surrounding the load during all stages of the process is important, and the medium should be kept in motion. Also, it is well known that removing moisture from the treated goods is more efficient if the moisture-transferring media can be kept efficiently in circulation. According to the prior art, this has been accomplished using fans. A fan in a sterilization chamber mostly requires a shaft penetrating the chamber wall, which leads to expensive technical solutions. Lubricants other than pure water are usually not allowed in sterilization chambers, and this fact puts requirements on the bearings. Magnet-coupled drives eliminate the shaft but not the bearing issue, and they are expensive.

In addition to proper medium distribution, a fan provides the dynamics required for penetration of gaseous medium into the crevices of the load.

In U.S. Pat. No. 2,713,702, a low-temperature autoclave is disclosed having a conventional steam jet aspirator discharging into the autoclave chamber. The system includes a return line from the chamber to the aspirator and is designed for providing intermittent injection of steam into the chamber to maintain a uniform, controlled temperature below 100° C. without creating a vacuum.

DISCLOSURE OF THE INVENTION

According to the present invention, the required movement of gas, steam and vapors within a batch treatment chamber using gas, steam or vapor is achieved using a gas ejector device located within the chamber and having an essentially straight secondary stream flow path through the ejector device. Ejectors are well known devices utilizing the energy of a primary fluid stream to create a secondary stream. This is based on the theory that a properly designed nozzle followed by a properly designed throat or venturi will economically make use of high pressure fluid to generate a flow. An ejector device may be used both for suction and blowing. Thus, a suitably located ejector device supplied with e.g. pressurized air will create a flow within a batch treatment chamber. The ejector device has no moving parts and thus eliminates the various problems described above associated with fan arrangements.

According to the invention, an apparatus for the treatment of objects with gas, steam or vapor is provided e.g. for sterilization, drying or cooling, said apparatus having at least one ejector device inside a closable chamber, said ejector device(s) having a straight flow path of the secondary stream through the ejector device.

The conventional fluid jet ejector utilizes a straight flow path for the primary stream and has a suction inlet on the side. According to the present invention, an ejector having a straight secondary stream flow path is used. An ejector device useful for the purposes of the present invention is the Ecojet Suction Conveying Nozzle manufactured by Krahnen GmbH, Köln, Germany; the device features a specially designed annular slit around the secondary stream flow channel for introducing the driving (primary) fluid, which is supplied from a side inlet. The secondary stream thus flows in a straight line through the device.

DETAILED DISCLOSURE

Figure 1:
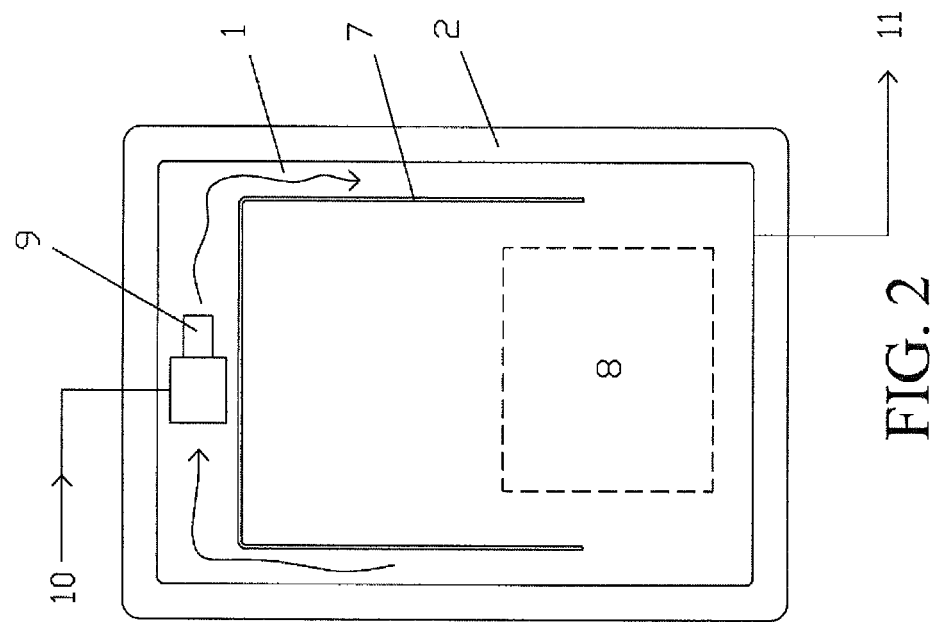
FIG. 1 is a schematic drawing of a sterilization chamber according to the prior art.

FIG. 1 is a schematic drawing of a prior art sterilization chamber provided with a fan arrangement. The apparatus features a pressure- and vacuum-capable chamber 1 with a jacket 2 for receiving heat transfer medium. Connections for steam, pressurized air and other commodities are provided, as well as outlets (neither shown in the figure). Above the load space, a turbine wheel 3 is fitted to a shaft 4 penetrating the wall and the jacket and driven by a motor 5. Lubrication is provided by WFI (water for injection) grade water at 6. Appropriate baffles 7 may be provided to distribute the flow of gases around and within the load 8. Gas flow caused by the turbine wheel is shown by arrows.

Figure 2:
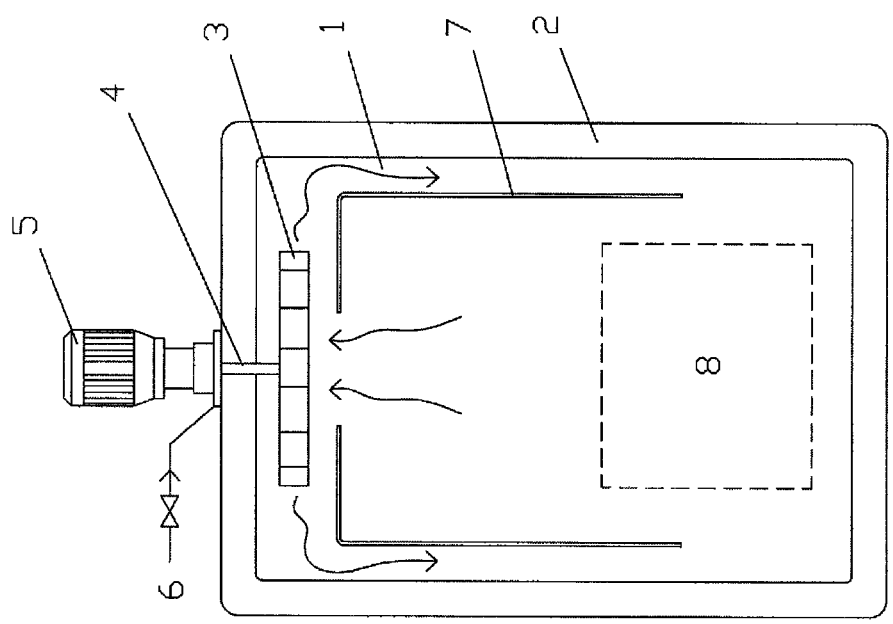
FIG. 2 is a corresponding drawing of a sterilization chamber according to the invention.

FIG. 2 depicts a corresponding sterilization chamber according to the present invention. An ejector device 9 is situated above the load space, and supplied with compressed air at 10. As the ejector operates, a fluid stream is generated as indicated by arrows, and causes a circulation flow within the chamber. In a constant pressure state, a stream corresponding to the supplied air stream is withdrawn from connection 11.

Several ejector devices may be used within the chamber to provide appropriate circulation. Positioning and directing of the ejectors to generate an optimal gas flow path is easily accomplished due to their design. Advantageously, for example, two ejectors may be mounted to a single T-tube.

A sterilizer is further provided with connections for steam, air at various pressures and venting, as well as drains for condensate. This applies both to chamber and jacket as required; these connections are not shown, neither is the instrumentation required for control and performance monitoring.

A sterilization process may include, for example, one or more initial vacuum stages to remove air and replace it with steam at high temperature. Subsequently may follow a period at maximum temperature, during which period steam is supplied as required.

A sterilization cycle may employ e.g. forced air removal and indirect cooling by circulating cooling medium in the sterilizer jacket. During heating, cooling or drying stages, circulation of the vessel atmosphere is routinely employed. Cooling water may also be introduced directly into the chamber by spraying. In a device according to the present invention, cooling medium may be supplied to the ejector device, either in the compressed air supply or e.g. through a separate nozzle to the secondary stream.

Any particular fluid or mixture of different fluids entering the chamber at any given stage of the process may be introduced via the ejector device in order to enhance the energy or material transfer process, either fed to the primary stream or separately to the secondary stream as described above. Various fluids employed in batch treatment processes may be set in motion using one or more ejector devices within the apparatus according to the invention. Such processes can utilize gaseous or liquid-vapor sterilizing agents, such as peroxides, e.g. hydrogen peroxide, peracetic acid or ethylene oxide.

The above description is mainly concerned with sterilization processes, but the arrangement according to the invention may be applied in, e.g., washing equipment for enhancing drying of the load after washing with liquid.

The invention claimed is:

1. A device for treating batches of objects with gas, steam or vapor, the device comprising a closable chamber for containing said objects and at least one ejector device for generating a secondary gas stream within the chamber by means of a primary gas stream, the at least one ejector device having no moving parts for generating the secondary gas stream, the at least one ejector device located within said chamber and the at least one ejector device including:
   a secondary flow channel having an inlet and an outlet in said chamber for drawing a secondary gas from said chamber and exhausting said secondary gas back into said chamber to generate said secondary gas stream within said chamber wherein the secondary gas flows through the at least one ejector device in an essentially straight line, and
   a second inlet fluidly connecting the secondary flow channel to a source of pressurized primary gas wherein the primary gas draws the secondary gas into the at least one ejector device through said inlet of said secondary flow channel.

2. The device according to claim 1, wherein the at least one ejector device has at least one connection for supplying steam, water or compressed air.

3. The device according to claim 1, wherein the at least one ejector device has at least one connection for supplying a chemical sterilizing agent.

* * * * *